(12) United States Patent
Miller

(10) Patent No.: US 9,675,791 B1
(45) Date of Patent: Jun. 13, 2017

(54) SPRING TENSIONER FOR TATTOO MACHINE NEEDLE

(71) Applicant: Adam Miller, Los Angeles, CA (US)

(72) Inventor: Adam Miller, Los Angeles, CA (US)

(73) Assignees: Michael Chen, Baldwin Park, CA (US); Wen Wei, Baldwin Park, CA (US); Billy Chen, Baldwin Park, CA (US)

( * ) Notice: Subject to any disclaimer, the term of this patent is extended or adjusted under 35 U.S.C. 154(b) by 743 days.

(21) Appl. No.: 14/144,529

(22) Filed: Dec. 30, 2013

(51) Int. Cl.
*A61B 17/34* (2006.01)
*A61M 37/00* (2006.01)

(52) U.S. Cl.
CPC ............... *A61M 37/0076* (2013.01)

(58) Field of Classification Search
CPC .......... A61M 37/0076; A61M 37/0084; A61M 37/0092; A01K 11/005
See application file for complete search history.

(56) References Cited

U.S. PATENT DOCUMENTS

| | | | | |
|---|---|---|---|---|
| 4,159,659 A | * | 7/1979 | Nightingale | A61M 37/0076 30/362 |
| 7,207,242 B1 | * | 4/2007 | Daigle | A61M 37/0076 30/362 |
| 2005/0028647 A1 | * | 2/2005 | Sloan | A61M 37/0076 81/9.22 |

* cited by examiner

*Primary Examiner* — Tuan V Nguyen
(74) *Attorney, Agent, or Firm* — Quickpatents, LLC; Kevin Prince

(57) ABSTRACT

An improvement to a tattoo machine of the type having an oscillating needle bar, a needle tube, a grip, and a needle tube support is either added to an existing tattoo machine or incorporated into the tattoo machine during manufacture. A tensioner base selectively fixable with the needle tube support comprises a support attachment and a spring support. A resilient tensioner spring is fixed with the spring support at a proximate end thereof. The tensioner spring terminates with a wheel support fixed to a distal end of the tensioner spring. The tensioner spring includes at least one curved portion between the ends, and at least two adjustment screw apertures therethrough. An adjustment screw is fixed with the tensioner spring to the spring support through the at least two adjustment screw apertures of the tensioner spring. A tensioner wheel is rotationally fixed with the wheel support of the tensioner spring.

17 Claims, 4 Drawing Sheets

SPRING TENSIONER FOR TATTOO MACHINE NEEDLE

CROSS-REFERENCE TO RELATED APPLICATIONS

Not Applicable.

STATEMENT REGARDING FEDERALLY SPONSORED RESEARCH AND DEVELOPMENT

Not Applicable.

FIELD OF THE INVENTION

This invention relates to tattoo machines, and more particularly to a spring tensioner for a tattoo needle.

DISCUSSION OF RELATED ART

Tattoo machines typically have a body, a motor fixed with an oscillating needle bar, a needle tube, a grip, and a needle tube support. In such a tattoo machine, the needle bar oscillates up and down within the needle tube. If the inside diameter of the needle tube is larger than the diameter of the tattoo needle, then the needle is subject to lateral, forward and backward instability, which can lead to loss of resolution in the tattooed image.

Traditionally tattoo artists have stretched a rubber band between the tattoo machine body and the needle bar to stabilize the needle bar between forward and backward movement, but such an arrangement still results in considerable lateral instability of the needle bar.

A tensioner wheel mechanism is included on several tattoo machines manufactured under the trademark Dragonfly by Ink Machines, Sweden AB. Such a tensioner wheel contacts the needle bar as it oscillates and includes a circumferential groove so as to impart lateral stability to the needle bar in addition to forward and backward stability. However, such a mechanism is somewhat complex and includes a plurality of parts, adding to the cost of such tattoo machines.

Therefore, there is a need for an improvement to a tattoo machines that imparts lateral stability to the needle bar in addition to forward and backward stability. Such a needed device would have relatively few parts and would therefore be relatively inexpensive to manufacture. Further, such a device would impart a spring-biased tension to the needle bar to absorb lateral forces imparted to the needle bar through the needle, as opposed to the customer's skin having to absorb such forces, sometimes painfully so. The present invention accomplishes these objectives.

SUMMARY OF THE INVENTION

The present device an improvement for a tattoo machine of the type having an oscillating needle bar, a needle tube, a grip, and a needle tube support. The tattoo machine further includes a body that supports a motor which is operatively connected with the needle bar to oscillate the needle bar when power is supplied to the motor. In such a tattoo machine, the needle bar oscillates up and down within the needle tube. In one embodiment the improvement is added to an existing tattoo machine. Alternately, the improvement is incorporated into the tattoo machine during manufacturing.

A tensioner base is selectively fixable with the needle tube support of the tattoo machine. The tensioner base comprises a support attachment and a spring support. Preferably the tensioner base is fixable with the needle tube support with a thumbscrew that traverses the tensioner base at an aperture therein and engages a threaded aperture of the needle tube support. The support attachment may also include a threaded aperture for receiving the adjustment screw.

A resilient tensioner spring is fixed with the spring support at a proximate end thereof. The tensioner spring terminates with a wheel support fixed to a distal end of the tensioner spring. The tensioner spring includes at least one curved portion between the ends, and at least two adjustment screw apertures therethrough. An adjustment screw is fixed with the tensioner spring to the spring support through the at least two adjustment screw apertures of the tensioner spring.

A tensioner wheel is rotationally fixed with the wheel support of the tensioner spring. The tensioner wheel preferably comprises a bearing assembly on the axle and a pair of stacked elastomeric O-rings. As such, the needle bar is positioned between the two O-rings so as to impart lateral stability to the needle bar when oscillating.

The present invention is an improvement to a tattoo machines that imparts lateral stability to the needle bar in addition to forward and backward stability. The improvement has relatively few parts and is therefore relatively inexpensive to manufacture. Further, such a device imparts a spring-biased tension to the needle bar to absorb lateral forces imparted to the needle bar through the needle, as opposed to the customer's skin having to absorb such forces. Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list. When the word "each" is used to refer to an element that was previously introduced as being at least one in number, the word "each" does not necessarily imply a plurality of the elements, but can also mean a singular element.

Figure 1:
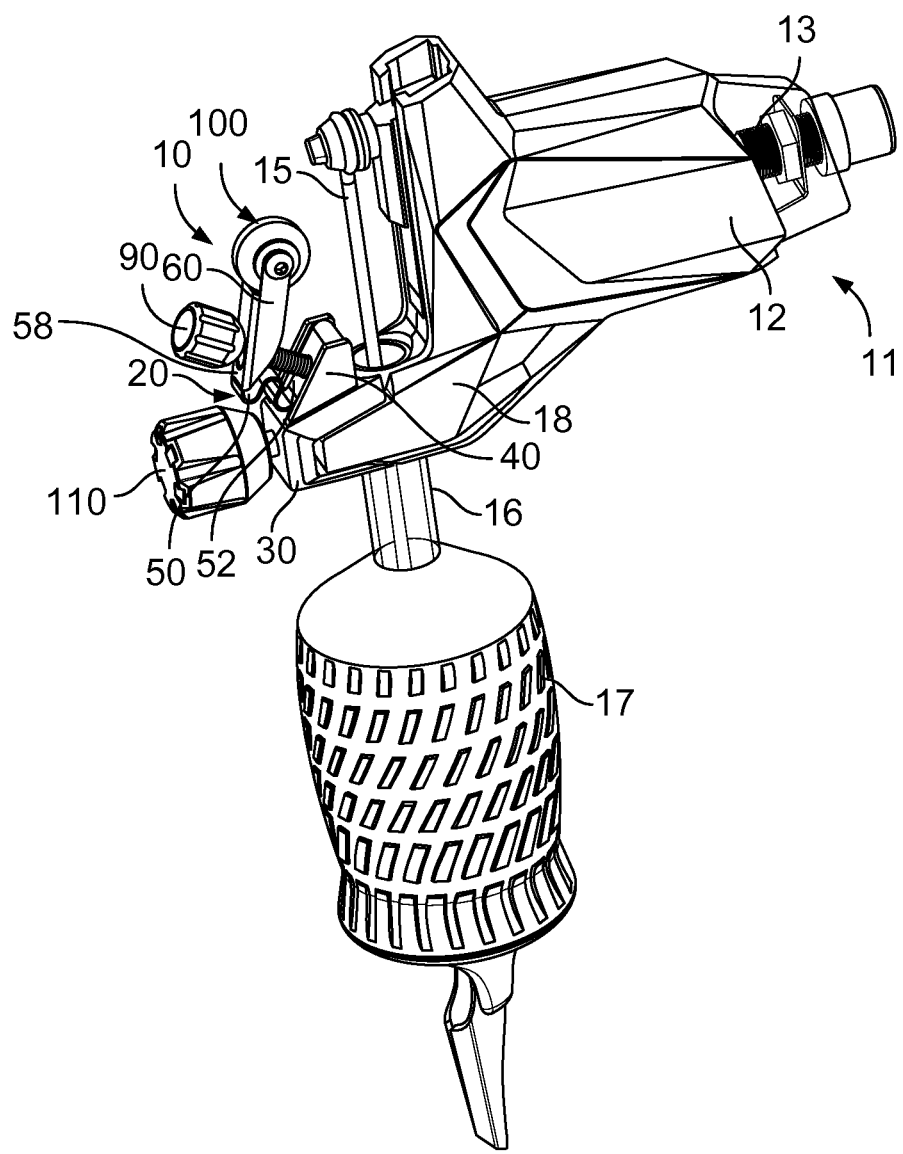
FIG. 1 is a perspective view of the invention as affixed with a tattoo machine.
Figure 2:
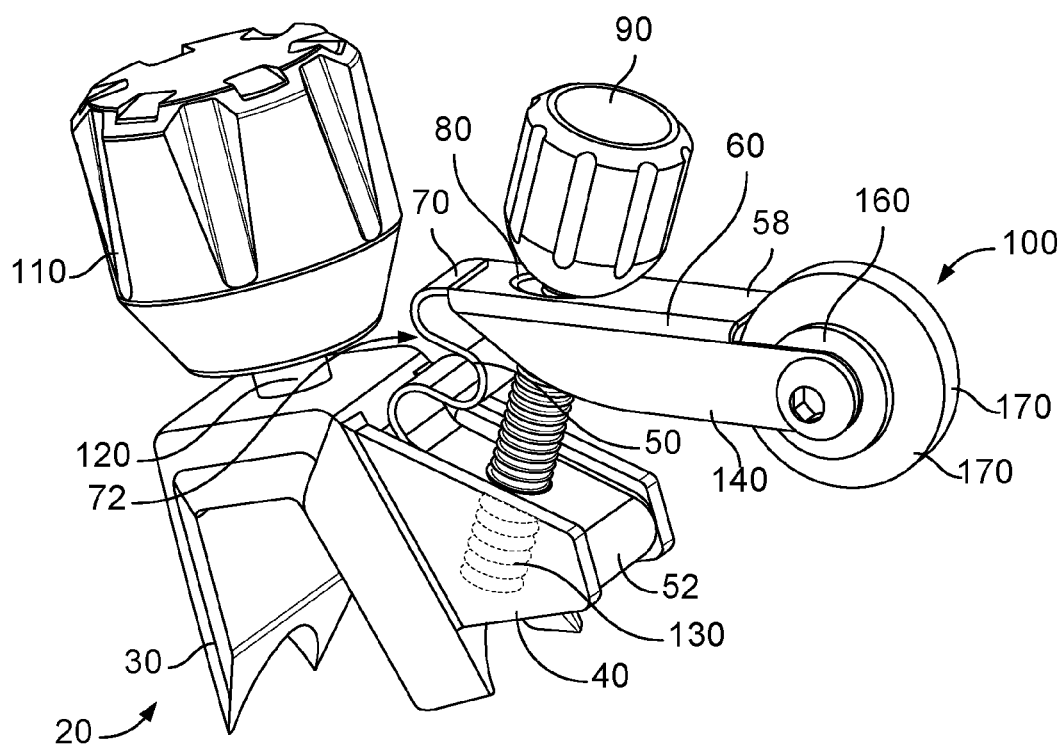
FIG. 2 is an enlarged perspective view of the invention.

FIGS. 1 and 2 illustrate an improvement 10 for a tattoo machine 11 of the type having an oscillating needle bar 15, a needle tube 16, a grip 17, and a needle tube support 18. The tattoo machine 11 further includes a body 12 that supports a motor 13 which is operatively connected with the needle bar 15 to oscillate the needle bar 15 when power is supplied to the motor 13. In such a tattoo machine 11, the needle bar 15 oscillates up and down within the needle tube 16. In one embodiment the improvement 10 is added to an existing tattoo machine 11. Alternately, the improvement 10 is incorporated into the tattoo machine 11 during manufacturing.

A tensioner base 20 is selectively fixable with the needle tube support 18 of the tattoo machine 11. The tensioner base 20 comprises a support attachment 30 and a spring support 40. Preferably the tensioner base 20 is made from either a rigid plastic or metal material, and is fixable with the needle tube support 18 with a thumbscrew 110 that traverses the tensioner base 20 at an aperture 120 therein and engages a threaded aperture of the needle tube support 18. Alternately, the tensioner base 20 is fixable with the tattoo machine body 12 with an alternate type of mechanical fastener, such as a snap-fit arrangement or the like (not shown). The support attachment 30 may also include a threaded aperture 130 for receiving the adjustment screw 90 (FIG. 2).

Figure 5:
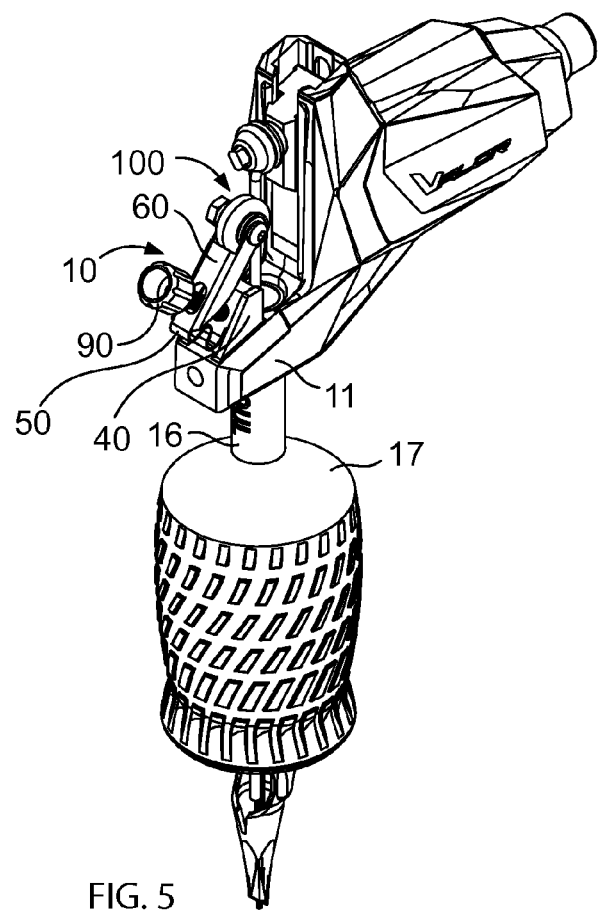
FIG. 5 is a perspective view of an alternate embodiment of the invention.

In one embodiment, just the spring support 40 is fixed to the tattoo machine 11 directly, eliminating the need for the tensioner base 20 and the support attachment 30 (FIG. 5). Such an embodiment is incorporated into the tattoo machine 11 during manufacturing.

Figure 4:
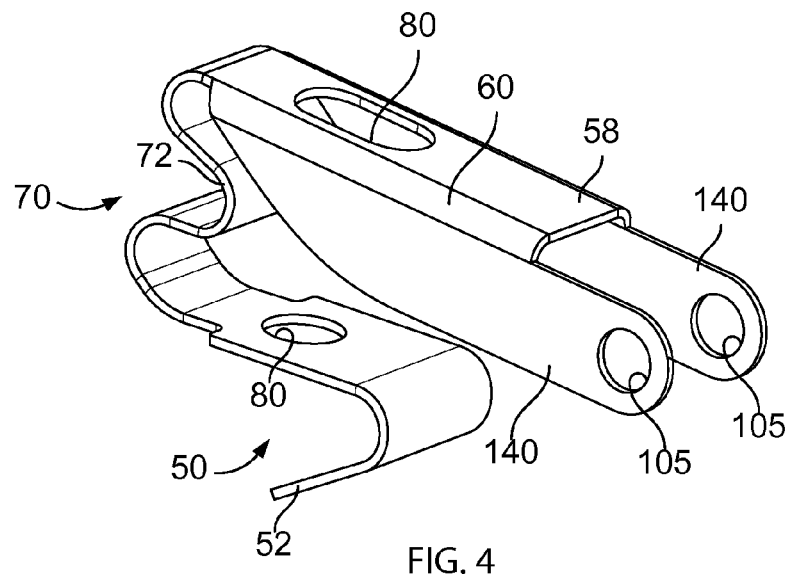
FIG. 4 is a perspective view of a tensioner spring and a wheel support of the invention.

A resilient tensioner spring 50 is fixed with the spring support 40 at a proximate end 52 thereof. The tensioner spring 50 terminates with a wheel support 60 fixed to a distal end 58 of the tensioner spring 50. The tensioner spring 50 includes at least one curved portion 70 between the ends 52,58 and at least two adjustment screw apertures 80 therethrough (FIG. 4). The curved portion 70 of the tensioner spring 50 comprises either a single U-shaped curved portion 71, or an M-shaped curved portion 72. In one embodiment the tensioner spring 50 is formed from 302½ hard stamped stainless steel, so-called "steel spring," or the like.

An adjustment screw 90 is fixed with the tensioner spring 50 to the spring support 40 through the at least two adjustment screw apertures 80 of the tensioner spring 50 (FIG. 4). Preferably the outermost of the adjustment screw apertures 80 is oval in shape so that the tensioner spring 50 can move between a compressed position and a relaxed position (not shown) without being constrained by the adjustment screw.

Figure 3:
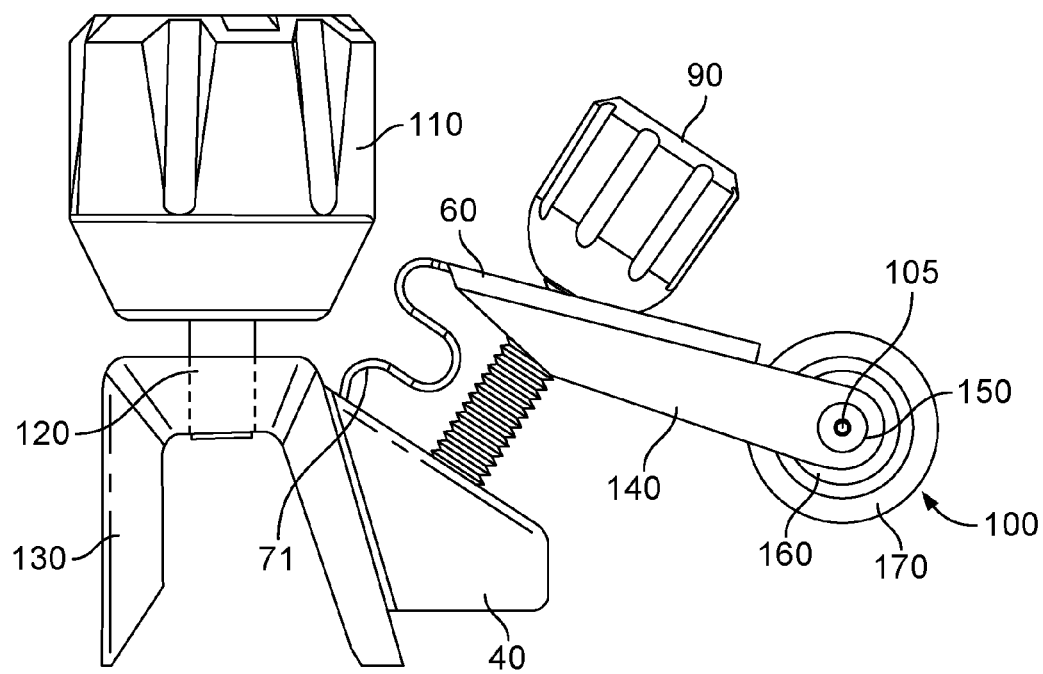
FIG. 3 is a side elevational view of FIG. 2.

A tensioner wheel 100 is rotationally fixed with the wheel support 60 of the tensioner spring 50. Preferably the wheel support 60 of the tensioner spring 50 comprises two wings 140 folded 90-degrees, each of which have an axle aperture 150 therethrough for rotationally fixing an axle 105 of the tensioner wheel 100 (FIGS. 3 and 4). The tensioner wheel 100 preferably comprises a bearing assembly 160 on the axle 105 and a pair of stacked elastomeric O-rings 170. As such, the needle bar 15 is positioned between the two O-rings 170 so as to impart lateral stability to the needle bar 15 when oscillating.

As such, the adjustment screw 90 may be tightened to compress the ends 52,58 of the tensioner spring 50 together and lower the tensioner wheel 100 towards the needle bar 15. Once making contact with the needle bar 15 the tensioner wheel 100 applies pressure to the needle bar 15 to stabilize same.

While a particular form of the invention has been illustrated and described, it will be apparent that various modifications can be made without departing from the spirit and scope of the invention. Accordingly, it is not intended that the invention be limited, except as by the appended claims.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. An improvement for a tattoo machine having an oscillating needle bar, a needle tube, a grip, and a needle tube support, the improvement comprising:
a tensioner base selectively fixable with the needle tube support, the tensioner base comprising a support attachment and a spring support;
a resilient tensioner spring fixed with the spring support at a proximate end thereof, the tensioner spring terminating at a wheel support at a distal end thereof, the tensioner spring including at least one curved portion between the ends and at least two adjustment screw apertures therethrough;
an adjustment screw fixing the tensioner spring with the spring support through the at least two adjustment screw apertures of the tensioner spring; and
a tensioner wheel rotationally fixed with the wheel support;
whereby the adjustment screw may be tightened to compress the ends of the tensioner spring together and lower the tensioner wheel towards the needle bar, whereby once making contact with the needle bar the tensioner wheel applies pressure to the needle bar to stabilize the needle bar.

2. The improvement of claim 1 wherein the tensioner base is fixable with the needle tube support with a thumbscrew that traverses the tensioner base at an aperture therein and engages a threaded aperture of the needle tube support.

3. The improvement of claim 1 wherein the support attachment includes a threaded aperture for receiving the adjustment screw therein.

4. The improvement of claim 1 wherein the wheel support of the tensioner spring comprises two wings folded 90-degrees, each having an axle aperture therethrough for rotationally fixing an axle of the tensioner wheel.

5. The improvement of claim 1 wherein the curved portion of the tensioner spring comprises a U-shaped curved portion.

6. The improvement of claim 1 wherein the curved portion of the tensioner spring comprises a M-shaped curved portion.

7. The improvement of claim 1 wherein an outermost of the adjustment screw apertures is oval in shape.

8. The improvement of claim 1 wherein the tensioner wheel comprises a bearing assembly on an axle and a pair of stacked elastomeric O-rings, the needle bar positioned between the two O-rings so as to impart lateral stability to the needle bar when oscillating.

9. A tattoo machine, comprising:
a body having a motor, an oscillating needle bar fixed with the motor, a needle tube, a grip, and a needle tube support;
a spring support fixed with the body;
a resilient tensioner spring fixed with the spring support at a proximate end thereof, the tensioner spring terminating at a wheel support at a distal end thereof, the tensioner spring including at least one curved portion between the ends and at least two adjustment screw apertures therethrough;
an adjustment screw fixing the tensioner spring with the spring support through the at least two adjustment screw apertures of the tensioner spring; and
a tensioner wheel rotationally fixed with the wheel support;
whereby the adjustment screw may be tightened to compress the ends of the tensioner spring together and lower the tensioner wheel towards the needle bar, whereby once making contact with the needle bar the tensioner wheel applies pressure to the needle bar to stabilize the needle bar.

10. The tattoo machine of claim 9 further including a tensioner base selectively fixable with the needle tube support, the tensioner base comprising a support attachment and the spring support.

11. The tattoo machine of claim 10 wherein the tensioner base is fixable with the needle tube support with a thumbscrew that traverses the tensioner base at an aperture therein and engages a threaded aperture of the needle tube support.

12. The tattoo machine of claim 10 wherein the support attachment includes a threaded aperture for receiving the adjustment screw therein.

13. The tattoo machine of claim 9 wherein the wheel support of the tensioner spring comprises two wings folded 90-degrees, each having an axle aperture therethrough for rotationally fixing an axle of the tensioner wheel.

14. The tattoo machine of claim 9 wherein the curved portion of the tensioner spring comprises a U-shaped curved portion.

15. The tattoo machine of claim 9 wherein the curved portion of the tensioner spring comprises a M-shaped curved portion.

16. The tattoo machine of claim 9 wherein an outermost of the adjustment screw apertures is oval in shape.

17. The tattoo machine of claim 9 wherein the tensioner wheel comprises a bearing assembly on an axle and a pair of stacked elastomeric O-rings, the needle bar positioned between the two O-rings so as to impart lateral stability to the needle bar when oscillating.

* * * * *